(12) United States Patent
Maione et al.

(10) Patent No.: US 10,441,625 B2
(45) Date of Patent: *Oct. 15, 2019

(54) MATERIALS AND METHODS FOR TREATMENT OF INFLAMMATION

(71) Applicant: Cytogel Pharma, LLC, Darien, CT (US)

(72) Inventors: Theodore E. Maione, Green Island, NY (US); Constantine Basil Maglaris, New Canaan, CT (US)

(73) Assignee: CYTOGEL PHARMA, LLC, Darien, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/035,274

(22) Filed: Jul. 13, 2018

(65) Prior Publication Data

US 2018/0311303 A1    Nov. 1, 2018

Related U.S. Application Data

(63) Continuation of application No. 13/113,392, filed on May 23, 2011, now abandoned.

(60) Provisional application No. 61/347,102, filed on May 21, 2010.

(51) Int. Cl.
*A61K 38/07* (2006.01)

(52) U.S. Cl.
CPC .................................. *A61K 38/07* (2013.01)

(58) Field of Classification Search
CPC ............ A61K 2039/55516; C07K 5/10; C07K 5/1016
See application file for complete search history.

(56) References Cited

U.S. PATENT DOCUMENTS

| | | | |
|---|---|---|---|
| 4,663,160 A | 5/1987 | Tsay et al. | |
| 5,410,016 A | 4/1995 | Hubbell et al. | |
| 6,107,358 A | 8/2000 | Harada et al. | |
| 6,303,578 B1 | 10/2001 | Zadina et al. | |
| 6,514,710 B1 | 2/2003 | Jones et al. | |
| 6,592,895 B2 | 7/2003 | Lang et al. | |
| 8,940,704 B2 * | 1/2015 | Maione ............... | C07K 5/10 514/21.9 |
| 2003/0068672 A1 | 4/2003 | Yu | |
| 2003/0139446 A1 | 7/2003 | Chen et al. | |
| 2003/0147835 A1 | 8/2003 | Munro et al. | |
| 2004/0266805 A1 | 12/2004 | Jessop et al. | |
| 2011/0065648 A1 | 3/2011 | Malone | |

FOREIGN PATENT DOCUMENTS

| | | |
|---|---|---|
| WO | 98/42732 A1 | 10/1998 |
| WO | 00/60956 | 10/2000 |
| WO | 2003/020304 A2 | 3/2003 |
| WO | 2006/068768 A2 | 6/2006 |
| WO | 2009/033740 A2 | 3/2009 |
| WO | 2009/076672 | 6/2009 |
| WO | 2011/034659 | 3/2011 |

OTHER PUBLICATIONS

Menkin Science 29:1026, (Year: 1954).*
Agnes et al., "Structure-Activity Relationships of Bifunctional Peptides Based on Overlapping Pharmacophores at Opioid and Cholecystokinin Receptors," Journal of Medicinal Chemistry., 2006, vol. 49, pp. 2868-2875.
Alstergren, P. et al., "Co-variation of neuropeptide Y, calcitonin gene-related peptide, substance P and Neurokinin A in joint fluid from patients with temporomandibular joint arthritis," Archives of Oral Biology, 1995, 40(2):127-135.
Bayer HealthCare "Aspirin FAQs" [online] published Apr. 27, 2007 [retrieved on Jan. 16, 2013]. Retrieved from the Internet: <http://web.archive.org/web/20070427220442/http://www.aspirin.com/faq_en.html>.
Border et al. "Induction of Membranous Nephropathy in Rabbits by Administration of an Exogenous Cationic Antigen" Journal of Clinical Investigation, 1982, vol. 69, pp. 451-461.
Börzsei et al., "Inhibitory Action of Endomorphin-1 on Sensory Neuropeptide Release and Neurogenic Inflammation in Rats and Mice," Neuroscience, 2008, vol. 152, No. 1, pp. 82-88.
Cardillo et al., "Endomorphin-1 Analogues Containing β-Proline Are μ-Opioid Receptor Agonists and Display Enhanced Enzymatic Hydrolysis Resistance", Journal of Medicinal Chemistry, 2002, vol. 45, pp. 2571-2578.
Cardillo et al., "Stability against enzymatic hydrolysis of endomorphin-1 analogues containing β-proline", Organic and Biomolecular Chemistry, 2003, vol. 1, pp. 1498-1502.
Chalmers, J. et al., "Hypertension Optimal Treatment (HOT) study: a brilliant concept, but a qualified success," Journal of Hypertension, 1998, 16:1403-1405.
Cho et al., "Clonazepam release from bioerodible hydrogels based on semi-interpenetrating polymer networks composed of poly(ε-caprolactone) and poly(ethylene glycol) macromer", International Journal of Pharmaceutics, 1999, vol. 181, No. 2, pp. 235-242.
Cornish, J. et al., "Trifluoroacetate, a contaminant in purified proteins, inhibits proliferation of osteoblasts and chondrocytes," American Journal of Physiology-Endocrinology and Metabolism, 1999, 277(5):E779-E783.
Cruise et al. "Characterization of permeability and network structure of interfacially photopolymerized poly(ethylene glycol) diacrylate hydrogels" Biomaterials, 1998, vol. 19, pp. 1287-1294.
Janecka et al., "Enzymatic degradation studies of endomorphin-2 and its analogs containing N-methylated amino acids", Peptides, 2006, vol. 27, No. 1, pp. 131-135.
Janecka et al., "Synthesis and antinociceptive activity of cyclic endomorphin-2 and morphiceptin analogs", Biochemical Pharmacology, 2005, vol. 71, No. 1-2, pp. 188-195.

(Continued)

*Primary Examiner* — Kimberly Ballard
*Assistant Examiner* — Stacey N MacFarlane
(74) *Attorney, Agent, or Firm* — Saliwanchik, Lloyd & Eisenschenk

(57) ABSTRACT

The subject invention pertains to peptides and salts thereof that are useful as anti-inflammatory agents and to compositions containing such peptides and salts as active ingredients. Specifically exemplified herein are endomorphin-1 peptide (EM-1), analogs and salts thereof, and uses for modulation of calcitonin gene-related peptide (CGRP) production and/or substance P (SP) and for treatment of inflammation, particularly neurogenic inflammation.

2 Claims, 5 Drawing Sheets

Specification includes a Sequence Listing.

(56) References Cited

OTHER PUBLICATIONS

Jeong et al., "Thermoreversible Gelation of DEG-PLGA-PEG triblock copolymer aqueous solutions", Macromolecules, 1999, vol. 32, No. 21, pp. 7064-7069.

Jessop, "Endomorphins as Agents for the Treatment of Chronic Inflammatory Disease," Biodrugs, 2006, vol. 20, No. 3, pp. 161-166.

Jessop et al.,"Endomorphins in Rheumatoid Arthritis, Osteoarthritis, and Experimental Arthritis," Annals of the New York Academy of Sciences, 2010, vol. 1193, pp. 117-122.

Khalil, Z. et al., "Modulation of peripheral inflammation by locally administered endomorphin-1," Inflammation Research, 1999, 48:550-556.

Lang et al. "Synthesis and structural analysis of functionalized poly($\epsilon$-caprolactone)-based three-arm star polymers" Journal of Polymer Science Part A: Polymer Chemistry, 2002, vol. 40, No. 8.pp. 1127-1141.

McDougall et al., "Attenuation of Knee Joint Inflammation by Peripherally Administered Endomorphin-1," Journal of Molecular Neuroscience, 2004, vol. 22, pp. 125-137.

McPherson, "A comparison of salts for the crystallization of macromolecules", Protein Science, 2001, vol. 10, No. 2, pp. 418-422.

Neumeyer et al., "New Opioid Designed Multiple Ligand from Dmt-Tic and Morphinan Pharmacophores," Journal of Medicinal Chemistry, 2006, vol. 49, pp. 5640-5643.

Peppas et al., "Hydrogels in pharmaceutical formulations", European Journal of Pharmaceutics and Biopharmaceutics, 2000, vol. 50, pp. 27-46.

Qiu et al., "Miscibility and crystallization of poly(ethylene oxide) and poly($\epsilon$-caprolactone) blends", Polymer, 2003, vol. 44, No. 10, pp. 3101-3106.

Roux et al., "Elimination and exchange of trifluoroacetate counterion from cationic peptides: a critical evaluation of different approaches," Journal of Peptide Science, 2008, 14:354-359.

Schiess et al., "The effects of CGRP on calcium transients of dedifferentiating cultured adult rat cardiomyocytes compared to non-cultured adult cardiomyocytes: possible protective and deleterious results in cardiac function," Peptides, 2005, 26:525-530.

Snider et al., "Procalcitonin and its Component Peptides in Systemic Inflammation: Immunochemical Characterization," Journal of Investigative Medicine, 1997, 45(9):552-560.

Watanabe et al., "Differential inhibitory effects of $\mu$-opioids on substance P- and capsaicin-induced nociceptive behavior in mice," Peptides, 2006, 27:760-768.

Wu et al. "Synthesis, characterization and drug release from three-arm poly($\epsilon$-caprolactone) maleic acid/poly(ethylene glycol) diacrylate hydrogels" Journal of Biomaterials Science. Polymer Edition, 2003, vol. 14, No. 8, pp. 777-802.

\* cited by examiner

SEQUENCE LISTING

<160> NUMBER OF SEQ ID NOS: 26

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Amidated Phenylalanine

<400> SEQUENCE: 1

Tyr Pro Trp Phe
1

<210> SEQ ID NO 2
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Amidated Phenylalanine

<400> SEQUENCE: 2

Tyr Pro Phe Phe
1

<210> SEQ ID NO 3
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Hydroxylated Phenylalanine

<400> SEQUENCE: 3

Tyr Pro Trp Phe
1

<210> SEQ ID NO 4
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Hydroxylated Phenylalanine

<400> SEQUENCE: 4

Tyr Pro Phe Phe
1

<210> SEQ ID NO 5
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (4)..(4)
<223> OTHER INFORMATION: Amidated Phenylalanine

<400> SEQUENCE: 5

```
Tyr Pro Trp Phe
1

<210> SEQ ID NO 6
<211> LENGTH: 4
<212> TYPE: PRT
<213> ORGANISM: Artificial Sequence
<220> FEATURE:
<223> OTHER INFORMATION: Synthetic mu-opiate receptor peptides

<400> SEQUENCE: 6

Tyr Pro Phe Phe
1

<210> SEQ ID NO 7
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Nitrosylated Tryptophan
<220> FEATURE:
<221> NAME/KEY: MISC_FEATURE
<222> LOCATION: (4)..(4)
<223> OTHER INFORMATION: Amidated Phenylalanine

<400> SEQUENCE: 7

Tyr Pro Trp Phe
1

<210> SEQ ID NO 8
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Nitrosylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 8

Tyr Pro Phe Phe
1

<210> SEQ ID NO 9
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 9

Tyr Pro Phe Phe
1
```

```
<210> SEQ ID NO 10
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 10

Tyr Pro Phe Phe
1

<210> SEQ ID NO 11
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 11

Tyr Pro Phe Phe
1

<210> SEQ ID NO 12
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (3)..(3)
<223> OTHER INFORMATION: Alkylated Phenylalanine
<220> FEATURE:
<221> NAME/KEY: MISC_FEATURE
<222> LOCATION: (4)..(4)
<223> OTHER INFORMATION: Amidated Phenylalanine

<400> SEQUENCE: 12

Tyr Pro Phe Phe
1

<210> SEQ ID NO 13
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: D-Lys
```

```
<400> SEQUENCE: 13

Tyr Xaa Trp Phe
1

<210> SEQ ID NO 14
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide

<400> SEQUENCE: 14

Tyr Lys Phe Phe
1

<210> SEQ ID NO 15
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine

<400> SEQUENCE: 15

Tyr Xaa Trp Phe
1

<210> SEQ ID NO 16
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine

<400> SEQUENCE: 16

Tyr Xaa Phe Phe
1

<210> SEQ ID NO 17
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
```

```
<223> OTHER INFORMATION: Nitrosylated Tryptophan

<400> SEQUENCE: 17

Tyr Lys Trp Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Nitrosylated Phenylalanine

<400> SEQUENCE: 18

Tyr Lys Phe Phe
1

<210> SEQ ID NO 19
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Nitrosylated Tryptophan

<400> SEQUENCE: 19

Tyr Xaa Trp Phe
1

<210> SEQ ID NO 20
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Nitrosylated Phenylalanine

<400> SEQUENCE: 20

Tyr Xaa Phe Phe
1
```

```
<210> SEQ ID NO 21
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 21

Tyr Lys Phe Phe
1

<210> SEQ ID NO 22
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Alkylated Phenylalanine

<400> SEQUENCE: 22

Tyr Xaa Phe Phe
1

<210> SEQ ID NO 23
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 23

Tyr Lys Phe Phe
1

<210> SEQ ID NO 24
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
```

```
<222> LOCATION: (2)..(2)
<223> OTHER INFORMATION: Ornathine
<220> FEATURE:
<221> NAME/KEY: MISC_FEATURE
<222> LOCATION: (3)..(3)
<223> OTHER INFORMATION: Alkylated Phenylalanine

<400> SEQUENCE: 24

Tyr Xaa Phe Phe
1

<210> SEQ ID NO 25
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 25

Tyr Lys Phe Phe
1

<210> SEQ ID NO 26
<211> LENGTH: 4
<212> TYPE: PRT
<213> ORGANISM: Artificial Sequence
<220> FEATURE:
<223> OTHER INFORMATION: Synthetic mu-opiate receptor peptides
<220> FEATURE:
<221> NAME/KEY: MISC_FEATURE
<222> LOCATION: (2)..(4)
<223> OTHER INFORMATION: Cyclic Peptide
<220> FEATURE:
<221> NAME/KEY: MISC_FEATURE
<222> LOCATION: (3)..(3)
<223> OTHER INFORMATION: Alkylated Phenylalanine

<400> SEQUENCE: 26

Tyr Lys Phe Phe
1
```

MATERIALS AND METHODS FOR TREATMENT OF INFLAMMATION

CROSS-REFERENCE TO RELATED APPLICATIONS

The subject application is a continuation of co-pending application Ser. No. 13/113,392, filed May 23, 2011; which claims the benefit of U.S. Provisional Application Ser. No. 61/347,102, filed May 21, 2010, which are hereby incorporated by reference in their entirety, including any figures, sequences, and/or tables.

The Sequence Listing for this application is labeled "As-filed_ST25.txt", which was created on May 23, 2011, and is 8 KB. The entire content is incorporated herein by reference in its entirety.

BACKGROUND OF INVENTION

Field of the Invention

The subject invention relates to uses of the endomorphin-1 peptide, analogs and salts thereof for treating and alleviating inflammation, in particular, neurogenic inflammation.

Description of the Related Art

Much research has been devoted to development of compounds having anti-inflammatory properties. Although certain methods and chemical compositions have been developed that aid in inhibiting or controlling inflammation, improved anti-inflammatory methods and compositions are needed.

Neuroinflammatory conditions are complex and poorly understood disease processes. Diseases or disorders associated with neurological inflammation include neurogenic inflammation, meningitis, septic shock, Down's syndrome, postischemic brain injury, HIV encephalopathy, Parkinson's disease, Alzheimer's disease, amyotrophic lateral sclerosis and multiple sclerosis.

Present therapies for inflammatory conditions, particularly neuroinflammation, are largely based on steroids and non-steroidal anti-inflammatory compositions. These compositions, however, are usually associated with a high incidence of unsatisfactory toxicity and poor efficacy.

Three different types of opiate receptors have been found: delta ($\delta$), kappa ($\kappa$) and mu ($\mu$). Endomorphin-1 peptide (EM-1) and analogs have been found to exhibit opiate-like activity by binding to the mu (morphine) opiate receptor. The major putative function for opiates is their role in alleviating pain. Other areas where opiates are well-suited for use in treatment are conditions relating to gastrointestinal disorders, schizophrenia, obesity, blood pressure, convulsions, and seizures. These peptides, however, have not previously been reported to play any role in inflammatory processes.

BRIEF SUMMARY

The present invention provides novel and advantageous therapeutic methods for treating inflammation, particularly neurogenic inflammation. The methods comprise administering, to a subject in need of such treatment, an effective amount of an isolated peptide or salt thereof, wherein the peptide has a general formula:

Tyr-$X_1$-$X_2$-$X_3$, wherein $X_1$ is Pro, D-Lys or D-Orn;

$X_2$ is Trp, Phe or N-alkyl-Phe, wherein alkyl has 1 to about 6 carbon atoms; and $X_3$ is Phe, Phe-$NH_2$, D-Phe, D-Phe-$NH_2$ or p-Y-Phe, wherein Y is $NO_2$, F, Cl or Br.

Advantageously, the methods of the present invention can be used to control over-production of calcitonin gene-related peptide (CGRP) in a subject.

In another embodiment, the subject invention provides methods to control over-production of Substance P (SP) in a subject.

The subject invention also provides pharmaceutical compositions, e.g. anti-neurogenic inflammatory compositions, containing as an active ingredient an effective amount, of one or more peptides according to the formula expressed above and a non-toxic, pharmaceutically-acceptable carrier or diluent.

The pharmaceutical compositions of the subject invention can further comprise other active compounds. Such other active compounds include, but are not limited to, anti-inflammatory compounds such as, for example, steroidal compounds, including hydrocortisone and the like; or non-steroidal anti-inflammatories, including acetylsalicylic acid (aspirin), ibuprofen, acetaminophen, indomethacin, and the like. The additional active ingredient(s) can also be antiviral, antibacterial, antifungal or other antimicrobial compounds or antitumor compounds.

The methods of the present invention are useful for treating conditions selected from, for example, inflammatory conditions associated with pain, osteoarthritis, inflammatory skin conditions, asthma, fibromyalgia, eczema, rosacea, migraine, psoriasis, intestinal inflammation, rheumatoid arthritis, neurogenic swelling, edema, bruises, burns, sunburn, meningitis, septic shock, allergy, and dermatitis.

BRIEF DESCRIPTION OF SEQUENCES

Figure 1:
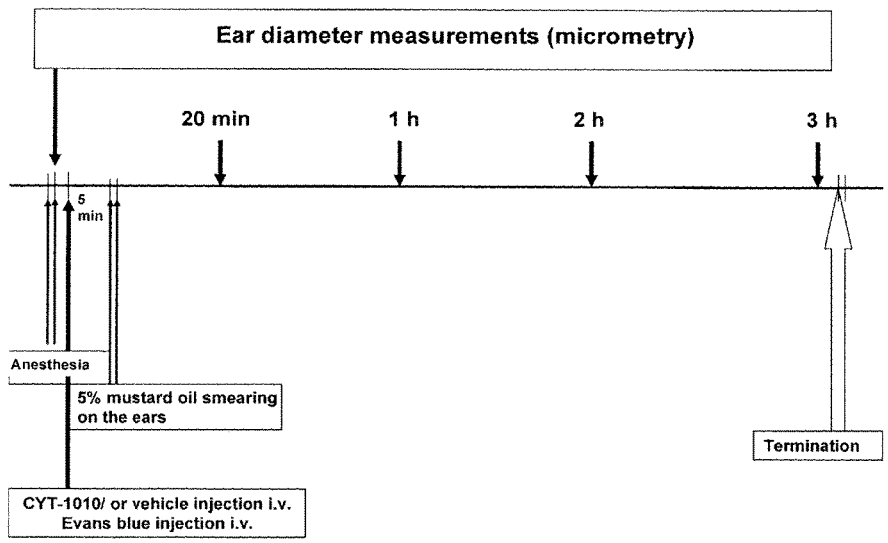
FIG. 1 is a schematic drawing describing an experimental protocol in rats.

SEQ ID NO:1 is a peptide useful according to the subject invention.
SEQ ID NO:2 is a peptide useful according to the subject invention.
SEQ ID NO:3 is a peptide useful according to the subject invention.
SEQ ID NO:4 is a peptide useful according to the subject invention.
SEQ ID NO:5 is a peptide useful according to the subject invention.
SEQ ID NO:6 is a peptide useful according to the subject invention.
SEQ ID NO:7 is a peptide useful according to the subject invention.
SEQ ID NO:8 is a peptide useful according to the subject invention.
SEQ ID NO:9 is a peptide useful according to the subject invention.
SEQ ID NO:10 is a peptide useful according to the subject invention.
SEQ ID NO:11 is a peptide useful according to the subject invention.
SEQ ID NO:12 is a peptide useful according to the subject invention.
SEQ ID NOS:13-26 are additional peptides useful according to the subject invention.

DETAILED DISCLOSURE

The subject invention pertains to novel uses as anti-inflammatory agents of endomorphin-1 peptide, analogs, and salts thereof. The peptides and compositions of the present invention are particularly effective in inhibiting neurogenic inflammation.

Peptides

In preferred embodiments, the present invention pertains to the use of peptides that have the general formula: Tyr-$X_1$-$X_2$-$X_3$, wherein $X_1$ is Pro, D-Lys or D-Orn; $X_2$ is Trp, Phe or N-alkyl-Phe, wherein alkyl has 1 to about 6 carbon atoms; and $X_3$ is Phe, Phe-$NH_2$, D-Phe, D-Phe-$NH_2$ or p-Y-Phe, wherein Y is $NO_2$, F, Cl or Br. Some preferred peptides of the invention are:

```
                                        (SEQ ID NO: 1)
H-Tyr-Pro-Trp-Phe-NH2

(SEQ ID NO: 2)
H-Tyr-Pro-Phe-Phe-NH2

(SEQ ID NO: 3)
H-Tyr-Pro-Trp-Phe-OH (SEQ ID NO: 4)
H-Tyr-Pro-Phe-Phe-OH (SEQ ID NO: 5)
H-Tyr-Pro-Trp-D-Phe-NH2

(SEQ ID NO: 6)
H-Tyr-Pro-Phe-D-Phe-NH2

(SEQ ID NO: 7)
H-Tyr-Pro-Trp-pNO2-Phe-NH2

(SEQ ID NO: 8)
H-Tyr-Pro-Phe-pNO2-Phe-NH2

(SEQ ID NO: 9)
H-Tyr-Pro-N-Me-Phe-Phe-NH2

(SEQ ID NO: 10)
H-Tyr-Pro-N-Et-Phe-Phe-NH2

(SEQ ID NO: 11)
H-Tyr-Pro-N-Me-Phe-D-Phe-NH2

(SEQ ID NO: 12)
H-Tyr-Pro-N-Et-Phe-D-Phe-NH2

(SEQ ID NO: 13)
H-Tyr-c-[D-Lys-Trp-Phe]

(SEQ ID NO: 14)
H-Tyr-c-[D-Lys-Phe-Phe]

(SEQ ID NO: 15)
H-Tyr-c-[D-Orn-Trp-Phe]

(SEQ ID NO: 16)
H-Tyr-c-[D-Orn-Phe-Phe]

(SEQ ID NO: 17)
fl-Tyr-c-[D-Lys-Trp-pNO2-Phe]
```

```
                                    (SEQ ID NO: 18)
        H-Tyr-c-[D-Lys-Phe-pNO2-Phe]

(SEQ ID NO: 19)
        H-Tyr-c-[D-Orn-Trp-pNO2-Phe]

(SEQ ID NO: 20)
        H-Tyr-c-[D-Orn-Phe-pNO2-Phe]

(SEQ ID NO: 21)
        H-Tyr-c-[D-Lys-N-Me-Phe-Phe]

(SEQ ID NO: 22)
        H-Tyr-c-[D-Orn-N-Me-Phe-Phe]

(SEQ ID NO: 23)
        H-Tyr-c-[D-Lys-N-Et-Phe-Phe]

(SEQ ID NO: 24)
        H-Tyr-c-[D-Orn-N-Et-Phe-Phe]

(SEQ ID NO: 25)
        H-Tyr-c-[D-Lys-N-Me-Phe-D-Phe]

(SEQ ID NO: 26)
        H-Tyr-c-[D-Lys-N-Et-Phe-D-Phe]
```

The last fourteen peptides listed are cyclic peptides whose linear primary amino acid sequences are given in SEQ ID NO:13 through SEQ ID NO:26. In this context, the applicants incorporate herein by reference, in its entirety, U.S. Pat. No. 6,303,578.

The peptide of SEQ ID NO:1 is highly selective and very potent for the .mu.opiate receptor, with over 4000-fold weaker binding to delta receptors and over 15,000-fold weaker binding to kappa receptors, thereby reducing the chances of side-effects.

The peptides of this invention may be prepared by conventional solution-phase (Bodansky, M., Peptide Chemistry: A Practical Textbook, $2^{nd}$ Edition, Springer-Verlag, New York (1993) or solid phase (Stewart, J. M.; Young, J. D. Solid Phase Peptide Synthesis, $2^{nd}$ edition, Pierce Chemical Company, 1984) methods with the use of proper protecting groups and coupling agents. A suitable deprotection method may then be employed to remove specified or all of the protecting groups, including splitting off the resin if solid phase synthesis is applied.

Cyclization of the linear peptides can be performed by, for example, substitution of an appropriate diamino carboxylic acid for Pro in position 2 in the peptides through ring closure of the 2-position side chain amino and the C-terminal carboxylic functional groups. The cyclization reactions can be performed with the diphenylphosphoryl azide method (Schmidt, R., Neuhert, K., *Int. J. Pept. Protein Res.* 37:502-507, 1991).

Peptides synthesized with solid phase synthesis can be split off the resin with liquid hydrogen fluoride (HF) in the presence of the proper antioxidant and scavenger.

The desired products may be isolated from the reaction mixture by crystallization, electrophoresis, extraction, chromatography, or other means. However, a preferred method of isolation is HPLC. All of the crude peptides can be purified with preparative HPLC, and the purity of the peptides may be checked with analytical HPLC. Purities greater than 95% of the synthesized compounds using HPLC have been obtained.

In a preferred embodiment specifically exemplified herein, the peptide is that which is shown as SEQ ID NO:13 (cyclic endomorphin-1 peptide) and has the following structure:

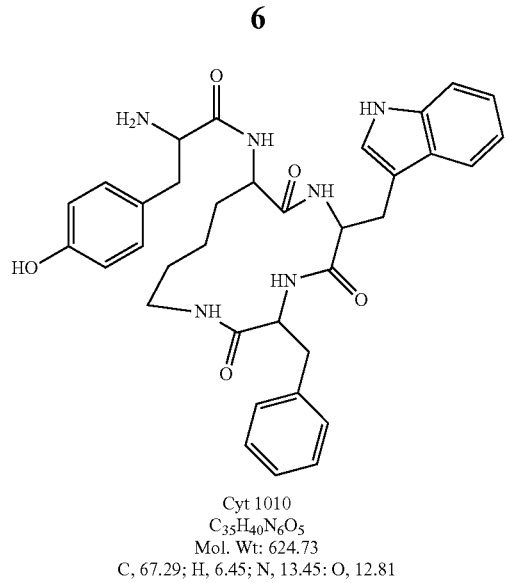

Cyt 1010
$C_{35}H_{40}N_6O_5$
Mol. Wt: 624.73
C, 67.29; H, 6.45; N, 13.45: O, 12.81

Surprisingly, it has now been discovered that endomorphin-1 peptide (EM-1) and analogs thereof can be used to modulate immune responses and alleviate inflammatory conditions, in particular, neurogenic inflammatory conditions and/or inflammatory conditions associated with pain. The peptides of the present invention are potent inhibitors of calcitonin gene-related peptide (CGRP) release in the peripheral and the central nervous systems. CGRP, expressed as CGRP-α and CGRP-β in humans, plays a pivotal role in autonomic, sensory, and motor activities via its interactions between the neurological, endocrine, and immune systems. It functions as a potent vasodilator and mediates the transmission of pain throughout the body.

CGRP expression is regulated, in part, by the expression of various immunomodulators such as cytokines, tumor necrosis factor-α (TNF-α), iNOS, and mitogen-activated protein kinases (MAPK). In turn, CGRP is also involved in the development and progression of inflammatory reactions, such as the accumulation of cAMP, T cell proliferation, and the secretion of interleukins such as IL-1 and IL-6 and cytokines in human blood monocytes. Serum concentrations of CGRP are markedly elevated in inflammation, systematic infections, joint disorders, and a variety of other diseases such as cardiac failure and hypertension. Particularly, CGRP is involved in many acute and chronic inflammatory reactions, such as for example, neurogenic inflammation, rheumatoid arthritis, sepsis, migraine, and endocrine diseases.

The release of CGRP from peptidergic afferents of isolated rat tracheae is evoked by electrical field stimulation (EFS) and its concentration can be determined from the incubation medium with radioimmunoassay. It has been found that EFS-induced CGRP release is significantly reduced by adding peptides of the present invention into the organ bath, during and after stimulation.

Furthermore, peptides of the present invention effectively suppress acute neurogenic inflammatory reactions in vivo. Neurogenic inflammation in the rat hindpaw skin and in the mouse ear is induced by activating sensory fibres with topical application of mustard oil. Plasma protein extravasation can be measured by Evans blue leakage and ear edema with micrometry. Mustard oil-induced plasma extravasation in the rat skin was significantly decreased by i.v. pretreatment with 1-1000 μg/kg CYT-1010, the lowest dose exerted, almost 60% inhibitory action. A similar significant anti-edema effect was also found on the mouse ear for these CYT-1010 doses throughout a 3-h period.

Treatment of Inflammation and Related Disorders

The peptides of the present invention, through administration to a subject, are useful for modulating immune responses and treating inflammation, particularly, neurogenic inflammation. The term "subject," as used herein, describes an organism, including mammals such as primates, to which treatment with the compositions according to the present invention can be administered. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters Advantageously, endomorphin-1 peptide and analogs thereof are powerful agents for treatment of inflammatory responses, including neurogenic inflammatory responses, through the inhibition of sensory neuropeptide release. The peptides of the present invention provide effective treatment for neurological inflammatory conditions, where nociceptor activation plays a pivotal role. At present, non-steroidal anti-inflammatory/analgesic drugs and corticosteroids are the most extensively used pharmaceuticals for neurological inflammation associated with nociceptor activation; however, these drugs, even in high doses, can only induce moderate inhibition of inflammatory responses.

In one embodiment, the present invention provides a method for treating inflammatory and immune conditions. The method comprises administering, to a subject in need of such treatment, an effective amount of endomorphin-1 peptide (EM-1), or an analog, and/or salt thereof. In a specific embodiment, the present method treats or ameliorates a condition associated with, at least in part, neuroinflammation or neurogenic inflammation. In another embodiment, the present method inhibits CGRP release, and is useful for treating, alleviating, or ameliorating a disease or condition associated with abnormal CGRP activity. In yet another embodiment, the methods of the subject invention can be used to inhibit SP release, and for treating a disease or condition associated with abnormal SP activity.

For purposes of the present invention, unless otherwise noted, the terms "inflammation" and "inflammatory response" include immune-related responses and/or allergic reactions to a physical, chemical, or biological stimulus. For example, inflammation for which the primary activating inflammation is antigen-derived can be due to, for example, bacterial lipopolysaccharide.

The term "neuroinflammation" or "neuroinflammatory diseases, disorders or conditions," as used herein, includes any disease, disorder or condition that is associated with the central and peripheral nervous systems, including inflammation that occurs in response to brain injury or autoimmune disorders, and inflammation that causes destruction of healthy neuronal and/or cerebral tissue.

"Neurogenic inflammation," as used herein, includes the local release of inflammatory mediators from afferent neurons such as substance P and calcitonin gene-related peptide.

Particularly exemplified herein is the use of the peptides and compositions of the present invention for treatment of neurogenic inflammation. Neurogenic inflammation can be evoked by neuropeptides, such as substance P (SP), calcitonin gene-related peptide (CGRP), vasoactive intestinal peptide (VIP), and neurokinin A (NKA), released from primary afferent C-fiber nerve terminals and histamine, secondarily released from mast cells (Dray, A., [1992] "Neuro pharmacological mechanisms of capsaicin and related substances" Biochem Pharm 44(4):611-15). In addition, it is known that capsaicin (CAP), the active constituent found in cayenne pepper, induces an acute neurogenic inflammatory response when applied topically to skin. CAP is a highly selective pain-producing substance that selectively stimulates nociceptive and thermal-sensitive nerve endings in tissues by acting on a specific membrane receptor. The mode of action of capsaicin, therefore, differs significantly from phorbol myristate acetate (PMA)-induced immune-inflammation. By comparison, PMA elicits its pro-inflammatory effects through cellular activation of specific immune cells such as macrophages.

The peptides and compositions of the present invention can be used to treat, alleviate, or ameliorate diseases and conditions associated with neurogenic inflammation including, but not limited to, osteoarthritis, asthma, fibromyalgia, eczema, rosacea, migraine, psoriasis, intestinal inflammation, rheumatoid arthritis, neurogenic swelling, edema, bruises, burns, sunburn, meningitis, septic shock, allergy, and dermatitis.

In addition, the peptides and compositions of the present invention can be used to treat, alleviate, or ameliorate inflammation at sites where the primary activating factor is antigen-derived (e.g. bacterial lipopolysaccharide) or of neurogenic origin. In one embodiment, the peptides of the subject invention are used to treat pathological inflammatory conditions of the brain.

In addition, the peptides and compositions of the present invention can be used to treat, alleviate, or ameliorate a variety of inflammatory skin conditions, in particular, skin conditions associated with inflammation and pain. The present invention can be used to treat, alleviate, or ameliorate inflammatory skin conditions including, but not limited to, radiation irritation and burns (including UV and ionizing), chemical burns, rhinitis, thermal burns, reddening of the skin, and chemically induced lesions. Additionally, the present invention can be used to treat, alleviate, or ameliorate a variety of inflammatory skin conditions, such as for example, atopic dermatitis, dermatitis, psoriasis, lichen simplex, acne, eczema, professional dermatitis, seborrheic dermatitis, prurigo nodularis, urticaria, keratosis, rosacea, erythema, ichtyosis, photodermatoses, shingles, and pruritic skin disorders. Additionally, the present invention can be used to treat, alleviate, or ameliorate inflammatory skin conditions caused by micro-organisms, chemicals, physical injury, environmental conditions, stress, aging, and autoimmune or inflammatory diseases. The peptides and compositions of the present invention are particularly useful to treat, alleviate, or ameliorate skin conditions including psoriasis, allergic contact dermatitis, eczema, urticaria, lichen planus, and dermatitis herpetiformis.

In addition, the peptides and compositions of the present invention can be used to treat, alleviate, or ameliorate allergic responses. This can include the use of the peptides in aerosol form for the treatment of acute allergic reactions such as acute asthmatic attack and in the treatment of inflammation of the lung caused by chemical exposure.

The peptides and compositions of the present invention are particularly useful to treat, alleviate, or ameliorate diseases and conditions associated with pain and inflammation including, but not limited to, inflammatory joints, muscles, tendons, nerves and skin; osteo-arthritis and rheumatoid arthritis; dermatitis; inflammatory bowel disease; post-operative pain and inflammation; general blunt trauma; bone injuries; soft tissue infections; and shingles.

In addition, the peptides and compositions of the present invention are particularly useful to treat, alleviate, or ameliorate diseases and conditions, such as for example, asthma, fibromyalgia, eczema, rosacea, migraine, psoriasis, intestinal inflammation, rheumatoid arthritis, neurogenic swelling, edema, bruises, burns, sunburn, meningitis, septic shock, allergy, and dermatitis.

Therapeutic Compositions and Formulations

The present invention further provides therapeutic compositions that contain a therapeutically effective amount of the peptides or salts and a pharmaceutically acceptable carrier or adjuvant. The present invention also contemplates prodrugs or metabolites of the peptides.

As used herein, the terms "pharmaceutically acceptable", "physiologically tolerable" and grammatical variations thereof, include compositions, carriers, diluents and reagents, are used interchangeably and represent that the materials are capable of administration to or upon a subject such as mammal.

The term "prodrug," as used herein, refers to a metabolic precursor of a compound of the present invention or pharmaceutically acceptable form thereof. In general, a prodrug comprises a functional derivative of a compound, which may be inactive when administered to a subject, but is readily convertible in vivo into an active metabolite compound.

Conventional procedures for the selection and preparation of suitable prodrug derivatives are described, for example, in "Design of Prodrugs", ed. H. Bundgaard, Elsevier, 1985. Preferably, a prodrug of the present invention enhances desirable qualities of the compound of the present invention including, but not limited to, solubility, bioavailability, and stability. Hence, the compounds employed in the present methods may, if desired, be delivered in a prodrug form. Prodrugs of the compounds employed in the present invention may be prepared by modifying functional groups present in the compound such that the modifications are cleaved, either in routine manipulation or in vivo, to the parent compound.

The term "metabolite," refers to a pharmacologically active product, including for example, an active intermediate or an ultimate product, produced through in vivo metabolism of a compound of the present invention in a subject. A metabolite may result, for example, from the anabolic and/or catabolic processes of the administered compound in a subject, including but not limited to, the oxidation, reduction, hydrolysis, amidation, deamidation, esterification, deesterification, enzymatic cleavage, and the like.

Metabolites are typically identified by preparing a radiolabelled (e.g., $^{14}C$ or $^{3}H$) isotope of a compound of the present invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to about 30 hours), and isolating its conversion products from the urine, blood or other biological samples. These products are easily isolated since they are labeled (others are isolated by the use of antibodies capable of binding epitopes surviving in the metabolite). The structure of metabolites can be determined in conventional fashion, e.g., by MS, LC/MS or NMR analysis. In general, analysis of metabolites is performed according to techniques well known to those skilled in the art of drug metabolism studies.

The peptide salts of the present invention may be compounded, for example, with the usual non-toxic, pharmaceutically acceptable carriers for tablets, pellets, capsules, liposomes, suppositories, intranasal sprays, solutions, emulsions, suspensions, aerosols, targeted chemical delivery systems (Prokai-Tatrai, K.; Prokai, L; Bodor, N., J. Med. Chem. 39:4775-4782, 1991), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, liquid or aerosol form, and in addition auxiliary, stabilizing, thickening and coloring agents and perfumes may be used.

In one embodiment, acids suitable for preparing the peptide salts are shown in Table 1, and the corresponding peptide salts are shown in Table 2. Preferred salt peptides include maleate salt, hydrochloride salt, lactate salt, aspartate salt, acetate salt, and trifluoro acetate salt.

TABLE 1

| Acids |
|---|
| Acetic |
| Aspartic (L) |
| Citric |
| Fumaric |
| Gluconic (D) |
| Hippuric |
| Hydrochloric |
| Lactic |
| Malic |
| Maleic |
| Mucic |
| Phosphoric |
| Sulfuric |
| Succinic |
| Tartaric (L) |

TABLE 2

| Salt Forms | | | |
|---|---|---|---|
| Acetate | Hippurate | Mucate | Tartrate (L) |
| Aspartate (L) | Hydrochloride | Phosphate | Gluconate (D) |
| Citrate | Lactate | Sulfate | Maleate |
| Fumarate | Malate (L) | Hemi-sulfate | Succinate |

The peptide salts of the subject invention can also be used to provide anti-inflammatory treatments. In this context the applicants incorporate herein by reference, in its entirety, U.S. 2004/0266805.

Further, the therapeutic composition can comprise one or more peptides or salts of the present invention as a first active ingredient, and one or more additional active ingredients comprising an anti-inflammatory compound known in the art. Such known anti-inflammatory drugs include, but are not limited to, steroidal anti-inflammatory drugs and non-steroidal anti-inflammatory drugs (NSAIDs), including acetylsalicylic acid (aspirin), ibuprofen, acetaminophen, indomethacin, and the like. The additional active ingredient(s) can be, for example, antiviral, antibacterial, antifungal or other antimicrobial compounds or antitumor compounds.

In accordance with one embodiment of the invention, therapeutically effective amounts of a known anti-inflammatory agent and the peptides of the present invention are administered sequentially or concurrently to a patient. The most effective mode of administration and dosage regimen of the peptides of the present invention and anti-inflammatory agent will depend upon the type of condition to be treated, the severity and course of that condition, previous therapy, the patient's health status, and response to the peptides of the present invention and the judgment of the treating physician. The present compositions may be administered to the patient at one time or over a series of treatments.

The present invention contemplates therapeutic compositions useful for practicing the therapeutic methods described herein. Therapeutic compositions of the present invention contain a physiologically tolerable carrier together with a therapeutically effective amount of a peptide as described herein, dissolved or dispersed therein as an active ingredient.

The peptides used in these therapies can also be in a variety of forms. These include for example, solid, semi-solid and liquid dosage forms, such as tablets, pills, powders, liquid solutions or suspensions, suppositories, injectable and infusible solutions. The preferred form depends on the intended mode of administration and therapeutic application.

The compositions also preferably include conventional pharmaceutically acceptable carriers and adjuvants which are known to those of skill in the art. Preferably, the compositions of the invention are in the form of a unit dose and will usually be administered to the patient one or more times a day.

The present peptides and compositions can be in a form that can be combined with a pharmaceutically acceptable carrier. In this context, the compound may be, for example, isolated or substantially pure. The term "carrier," as used herein, refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plants as they exist in nature.

The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The peptides of the present invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The active ingredient can be mixed with excipients which are pharmaceutically acceptable and compatible with the active ingredient and in amounts suitable for use in the therapeutic methods described herein. Suitable excipients are, for example, water, saline, dimethylsulphoxyde (DMSO) cyclodextrins, dextrose, glycerol, ethanol, sucrose, glucose, mannitol, sorbitol or the like and combinations thereof. In addition, if desired, the composition can contain minor amounts of auxiliary substances such as wetting or emulsifying agents, pH buffering agents and the like which enhance the effectiveness of the active ingredient. Particularly preferred excipients for peptides and compositions of the present invention include dimethylsulphoxyde (DMSO), and hydroxypropyl-β-cyclodextrin.

Liquid compositions also can contain liquid phases in addition to and to the exclusion of water. Exemplary of such additional liquid phases are glycerin, vegetable oils such as cottonseed oil, and water-oil emulsions.

The invention also provides a pharmaceutical pack or kit comprising one or more containers filled with one or more of the ingredients, e.g., compound, carrier suitable for administration.

Routes of Administration

The peptides and compositions of the present invention can be administered to the subject being treated by standard routes, including the oral, ophthalmic nasal, topical, transdermal, intra-articular, parenteral (e.g., intravenous, intraperitoneal, intradermal, subcutaneous or intramuscular), intracranial, intracerebral, intraspinal, intravaginal, intrauterine, or rectal route. Depending on the condition being treated, one route may be preferred over others, which can be determined by those skilled in the art.

For instance, the peptides and compositions of the present invention can be topically administered to the subject for treatment of conditions associated with skin inflammation. Compositions for topical administration can be in any of a variety of forms, including suspension, dispersion, solution, ointment, gel, cream, spray, foam, powder, lotion, soak, transdermal patch, solid, micro-particle, vapor, or tape.

The peptides of the present invention may also be administered utilizing liposome technology, slow release capsules, implantable pumps, and biodegradable containers. These delivery methods can, advantageously, provide a uniform dosage over an extended period of time. The amount of the therapeutic composition of the invention which is effective in the treatment of a particular disease, condition or disorder will depend on the nature of the disease, condition or disorder and can be determined by standard clinical techniques.

The dosage of effective amount of the peptides varies from and also depends upon the age and condition of each individual patient to be treated. In general, suitable unit dosages may be between about 0.01 to about 500 mg, about 0.01 to about 400 mg, about 0.01 to about 300 mg, about 0.01 to about 200 mg, about 0.01 to about 100 mg, or about 0.01 to about 50 mg. For example, a unit dose may be from between about 0.2 mg to about 50 mg. Such a unit dose may be administered more than once a day, e.g. two or three times a day.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In one embodiment, the peptides of the present invention and any second anti-inflammatory agent are administered sequentially to the patient, with the anti-inflammatory agent being administered before, after, or both before and after treatment with the peptides of the present invention. Sequential administration involves treatment with the anti-inflammatory agent at least on the same day (within 24 hours) of treatment with peptides of the present invention and may involve continued treatment with the anti-inflammatory agent on days that the peptides of the present invention is not administered.

Conventional modes of administration and standard dosage regimens of anti-inflammatory agents may be used (see Gilman, A. G. et. al. [eds] The Pharmacological Basis of Therapeutics, pp. 697-713, 1482, 1489-1491 [1980]; Physicians Desk Reference, 1985 Edition). For example, indomethacin can be administered orally at a dosage of about 25-50 mg, three times a day. Higher doses can also be used. Alternatively, aspirin (about 1500-2000 mg/day), ibuprofen (about 1200-3200 mg/day), or conventional therapeutic doses of other anti-inflammatory agents can be used. Dosages of anti-inflammatory agents can be titrated to the individual patient.

In addition, the patient may receive concurrent treatments with the anti-inflammatory agents and compositions comprising the peptide of the present invention. For example, the peptide of the present invention can be administered via local intralesional, or intravenous injection (see Gilman et. al. supra at pp. 1290-91). The anti-inflammatory agent can also administered by subcutaneous injection, intravenous injection, or orally.

Alternatively, the patient can receive a composition comprising a combination of one or more peptides of the present invention and an anti-inflammatory agent according to conventional modes of administration of agents which exhibit antibacterial, anticancer, antitumor or anti-inflammatory activity. These include, for example, parenteral, subcutaneous, intravenous, or intralesional routes of administration.

Materials and Methods

CYT-1010 (synthetic cyclized endomorphin-1 analog; FP014; Lot #: 080811-R2; Bottle H22; MW:684), was purchased from AmbioPharm, Inc. (North Augusta, S.C. 29812). Additional materials include: 2-hydroxypropyl-βcyclodextrin (HPCD; CY2005.5; CYL-3122), purchased from Cyclolab Ltd., Budapest, Hungary; Na-thiopental (Thiopental-Sandoz), purchased from Sandoz, Kundl, Austria; urethane, purchased from Spektrum 3D, Debrecen, Hungary; ketamine (Calypsol), purchased from Richter-Gedeon Ltd., Budapest, Hungary; xylazine (Xylavet), purchased from Phylaxia-Sanofi, Veterinary Biology Co. Ltd., Budapest, Hungary; rat α-CGRP, Tyr-α-CGRP(23-37), purchased from Bachem, Bubendorf, Switzerland; $^{125}$I-labelled SP, purchased from Amersham, International, Amersham, UK; $^{125}$I-labelled Tyr-α-CGRP(23-37), prepared in the laboratory of the Department of Pharmacology and Pharmacotherapy, University of Pécs, Hungary; allylisothiocyanate (mustard oil), Evans blue dye, purchased from Sigma, St. Louis, Mo., USA; paraffin oil, formamide, dimethylsulphoxyde (DMSO), purchased from Szkarabeusz Ltd., Pécs, Hungary.

Preparation of Solutions and Suspensions

For the in vitro release experiments, a 10 mg/ml (14.62 mM; MW 684) stock solution of CYT-1010 was made in DMSO, which was further diluted with the oxygenated Krebs solution used in the organ bath: 5.5 µl of this CYT-1010 stock solution was added into 40 ml Krebs to make the highest applied 2 µM concentration of compound CYT-1010. Further dilutions to obtain the lower concentrations were prepared with Krebs solution.

The incubation media containing the respective CYT-1010 concentrations were administered in the stimulated and post-stimulated 8-min fractions.

Since even the highest, 2 µM, concentration of CYT-1010 solution contained negligible amount of DMSO, simple Krebs solution was used in the control experiments.

For the in vivo rat and mouse experiments, 5.5 ml of the 1 mg/ml stock solution of CYT-1010 was prepared freshly every experimental day with 20% HPCD dissolved in sterile distilled water. This milky white micro-suspension was shaken and sonicated. The vehicle was 20% HPCD dissolved in sterile distilled water. Further dilutions of the compound for the smaller administered doses were made with this vehicle, the 500 µg/ml and 100 µg/ml concentrations looked opalescent and the lower concentrations were clear. In rats 0.1 ml/100 g, in mice 0.1 ml/10 g volumes were administered i.v. 10 min before the induction of the inflammation.

Induction of Sensory Neuropeptide Release from Isolated Rat Trachea by Electrical Field Stimulation (EFS)

Experimental Model

Rats were exsanguinated in deep anaesthesia (sodium thiobarbital, 50 mg/kg i.p.), then the whole trachea was removed and cleaned of fat and adhering connective tissues. Tracheae from two rats were placed into the same 1.8 ml organ bath to obtain sufficient amount of released peptide and perfused (1 ml/min) with pH-(7.2) controlled oxygenized Krebs solution for 60 minutes (equilibration period) at 37° C. temperature. After discontinuation of the flow, the solution was changed three times for eight minutes to produce pre-stimulated, stimulated, post-stimulated fractions.

Electrical field stimulation (40 V, 0.1 ms, 10 Hz for 120 s; 1200 pulses) was performed to elicit neurotransmitter release at the beginning of the second 8-minute period. Stimulation with 0.1 ms pulse width selectively activates very fast $Na^+$ channels, which are only present in the membrane of neural structures (Birmingham and Wilson, 1963; Coburn and Tomita 1973; Szolcsányi and Barthó, 1982); therefore, it excites nerve endings without influencing other excitable cells in the tracheae such as smooth muscle cells.

Protocol

Krebs solution was used in the pre-stimulated fraction for determining the basal CGRP outflow. During the stimulated and post-stimulated fractions, the incubation medium contained the examined concentrations of CYT-1010 (10, 100, 500, 1000 and 2000 nM) in separate experiments, and only one concentration was applied to the same tracheae to avoid neuropeptide depletion. In each group, 5 experiments were performed in parallel in 5 perfusion systems to provide n=5 data per group (10 tracheae per group).

Animals 60 male Wistar rats (250-300 g) altogether were divided into 6 experimental groups: Group 1: controls (n=10); Group 2: 10 nM CYT-1010 (n=10); Group 3: 100 nM CYT-1010 (n=10); Group 4: 500 nM CYT-1010 (n=10); Group 5: 1000 nM CYT-1010 (n=10); and Group 6: 2000 nM CYT-1010 (n=10). The total study was performed on three experimental days, two groups every occasion.

Investigational Technique: Measurement of CGRP and SP Concentrations by Radioimmunoassay Calcitonin gene-related peptide (CGRP) and substance P (SP) concentrations were determined from 400-400 μl samples of organ fluid of the preparations by means of radioimmunoassay methods described in Nemeth et al., 1996, 1998, 1999, 2006; Helyes et al., 1997, 2001, 2006; Borzsei et al., 2008). Each of these publications is incorporated herein by reference in its entirety.

The released amount of the peptides CGRP and SP was calculated as fmol peptide per mg wet tissue (trachea). The absolute release in response to EFS in each experiment was calculated by adding peptide release in the second and third 8-min fractions and then taking off the basal release measured in the first (pre-stimulated) fraction. The detection limits of the RIA assays were 0.2 fmol/tube and 2 fmol/tube for CGRP and SP, respectively.

Induction of Acute Neurogenic Inflammation in the Mouse Ear by Mustard Oil

Experimental Model

Mice were anaesthesized with urethane (1.2 g/kg i.p.) to achieve a long-lasting deep anaesthesia and minimize respiratory depression. Ten μl of 5% mustard oil dissolved in paraffin oil was smeared on both sides of both ears. Mustard oil in this concentration selectively activates Transient Receptor Potential A1 (TRPA1) on capsaicin-sensitive peptidergic sensory nerves and induces the release of sensory neuropeptides. The released CGRP and substance P (SP) in the innervated area evoke vasodilatation and plasma protein extravasation, collectively called as acute neurogenic inflammation.

Protocol

CYT-1010 (1, 10, 100, 500 and 1000 μg/kg; 0.1 ml/10 g from the 0.1, 1, 10, 50 and 100 μg/ml solutions) was administered i.v. 5 min before the induction of the inflammation by mustard oil smearing. Mice in the control group were treated with the same volume of the vehicle, 20% hydroxypropyl-β-cyclodextrin dissolved in sterile distilled water. The experimental protocol is also illustrated in FIG. 1.

Animals

There were 8 mice in each CYT-1010-treated experimental group, and 9 in the vehicle-treated control group. 49 male CD1 mice (25-35 g) altogether were divided into 6 experimental groups: Group 1: vehicle-treated controls (n=9); Group 2: 1 μg/kg CYT-1010 (n=8); Group 3: 10 μg/kg CYT-1010 (n=8); Group 4: 100 μg/kg CYT-1010 (n=8); Group 5: 500 μg/kg CYT-1010 (n=8); and Group 6: 1000 μg/kg CYT-1010 (n=8).

This study was undertaken in blocks with 12-13 mice per occasion. The whole set of data was obtained during 4 days. There were 2 or 3 solvent-treated rats every day and the remaining 12 animals were randomised to receive each treatment.

Investigational Technique: Measurement of Mouse Ear Swelling with Micrometry

The diameter of the ear was measured with an engineers' micrometer before the treatment and 4 times during the 3 h-examination period (20 min, 1 h, 2 h and 3 h). Oedema was expressed in % compared to the initial control values (Banvolgyi et al., 2004, 2005; Borzsei et al., 2008). Each of these publications is incorporated herein by reference in its entirety.

Induction of Acute Neurogenic Inflammation in the Paw Skin of the Rat by Mustard Oil Experimental Model Both hindlegs of the rats were acutely denervated (the sciatic and the saphenous nerves were cut 30 min before the induction of inflammation) under deep sodium thiopental (50 mg/kg i.p.) anaesthesia to avoid central reflexes. Acute neurogenic inflammation in the dorsal skin of the hindpaws was evoked by topical application of 1% mustard oil (allylisothiocianante) dissolved in paraffin oil. Mustard oil in concentrations below 5% selectively stimulates TRPA1 ion channels on capsaicin-sensitive peptidergic nerves and induces the release of pro-inflammatory sensory neuropeptides such as CGRP and substance P, which cause vasodilation and plasma protein extravasation in the innervated area.

Protocol

Figure 2:
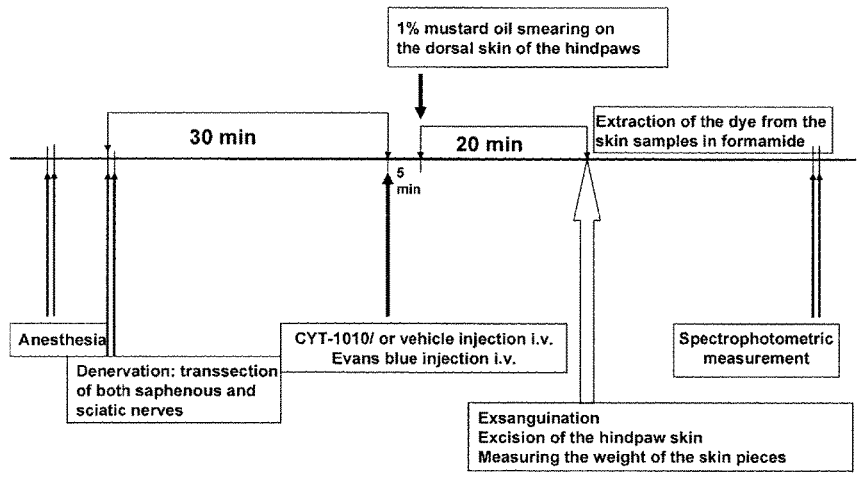
FIG. 2 is a schematic drawing describing an experimental protocol in rats.

CYT-1010 (1, 10, 100 and 1000 μg/kg; 0.1 ml/100 g from the 1, 10, 100 and 1000 μg/ml solutions) was administered i.v. 5 min before the induction of the inflammation by mustard oil smearing. Rats in the control group were treated with the same volume of the vehicle, 20% hydroxypropyl-β-cyclodextrin (dissolved in sterile distilled water). The experimental protocol is also illustrated in FIG. 2.

Animals 40 male Wistar rats (220-260 g) altogether were divided into 5 experimental groups: Group 1: 8 vehicle-treated controls (n=8); Group 2: 1 μg/kg CYT-1010 (n=8); Group 3: 10 μg/kg CYT-1010 (n=8); Group 4: 100 μg/kg CYT-1010 (n=8); and Group 5: 1000 μg/kg CYT-1010 (n=8).

This study was undertaken in blocks with 10 rats per occasion. The whole set of data was obtained during 4 days, and there were rats of each group every day.

Investigational Technique: Measurement of Evans Blue Accumulation in the Paw Skin Extravasation of plasma albumin was measured by the Evans blue leakage method. Evans blue (50 mg/kg) was injected i.v. and neurogenic inflammation was induced 10 min later. Rats were killed by exsanguination 20 min after mustard oil application. The skin of the hindpaws was removed and the extravasated dye was extracted with formamide for 72 h at room temperature for photometric determination at 620 nm. The amount of the accumulated Evans blue, which quantitatively correlates with the intensity of plasma extravasation, was expressed as μg dye/g wet tissue (Szolcsányi and Barthó 1981; Helyes et al., 1997, 2001, 2006). Each of these publications is incorporated herein by reference in its entirety.

Anesthesia

In the first series of the in vivo experiments of mice, ketamine (100 mg/kg, i.p.) and xylazine (10 mg/kg, i.m.) were used for anesthesia according to the conventional protocol. This time all the 10 mice died promptly, within 5 minutes after i.v. CYT-1010 injection, presumably due to respiratory depression; The 2 vehicle-treated animals survived. Therefore, urethane (1.2 g/kg i.p.) anaesthesia was chosen in this model, and in the further studies all mice survived except one in the 1 μg/kg dose group (this one has been replaced later to have the n=8 in each group).

Statistical Analysis

Results are expressed as the mean±s.e.m. and analyzed for statistical significance with one-way ANOVA followed by Dunnett post-hoc test when the data were compared to the control group. In the rat in vivo studies, multiple comparisons were also made with Bonferroni's modified t-test to compare the effects of the different doses to each other. *$p<0.05$ was considered to be significant. All individual data are tabulated in Tables 3-5.

Following are examples that illustrate procedures for practicing the invention. These examples should not be construed as limiting.

EXAMPLE 1

Effect of CYT-1010 on Electrical Field Stimulation-Evoked Release of CGRP and SP from Isolated Rat Tracheae This Example demonstrates that CTT-1010 inhibits release of the EFS-induced pro-inflammatory sensory neuropeptide CGRP and SP.

Figure 3:
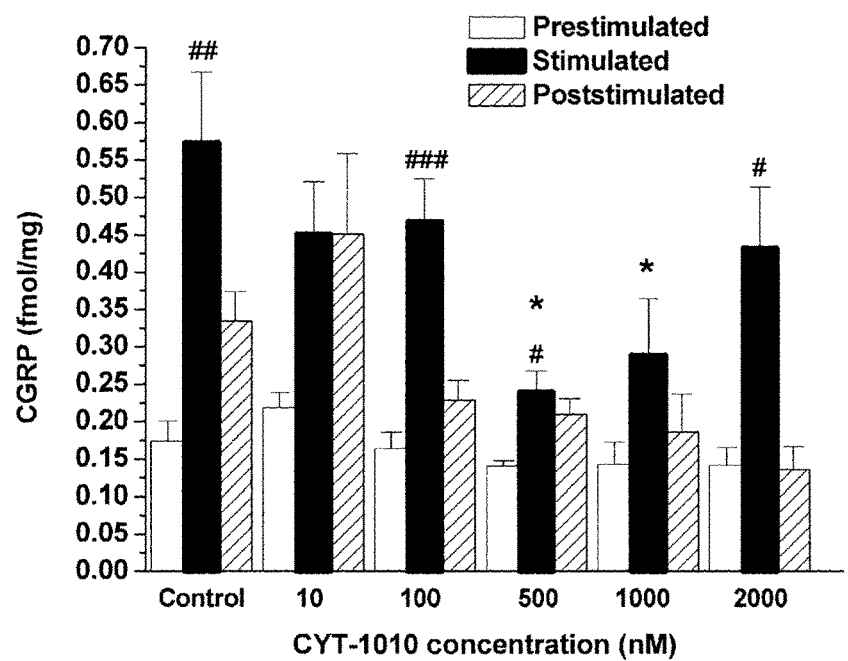
FIG. 3 shows the effect of CYT-1010 on electrically-evoked release of CGRP from isolated rat tracheae. Each column represents the mean±s.e.m. concentration of CGRP measured in the incubation medium of the pre-stimulated, stimulated and post-stimulated 8-min fractions of n=5 experiments (5×2 tracheae). *$P<0.05$ (vs. respective fraction of the vehicle-treated control experiment) and #$P<0.05$, ##$P<0.01$, ###$P<0.001$ (vs. pre-stimulated fraction of the respective experiment). Statistical analysis was performed with one-way ANOVA followed by Dunnett post-hoc test.
Figure 4:
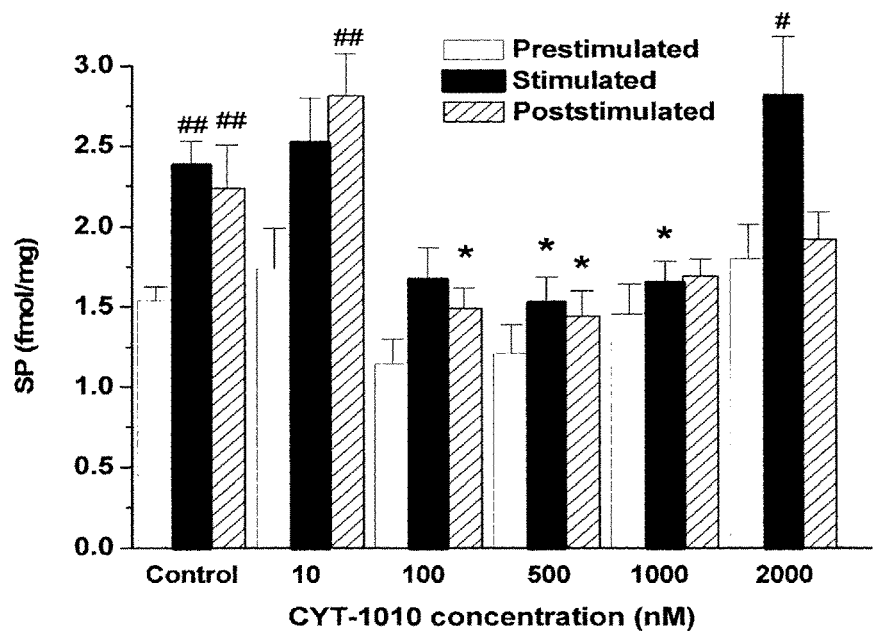
FIG. 4 shows the effect of CYT-1010 on electrically-evoked release of SP from isolated rat tracheae. Each column represents the mean±s.e.m. concentration of SP measured in the incubation medium of the prestimulated, stimulated and poststimulated 8-min fractions of n=5 experiments (5×2 tracheae). *$P<0.05$ (vs. respective fraction of the vehicle-treated control experiment) and #$P<0.05$, ##$P<0.01$, ###$P<0.001$ (vs. prestimulated fraction of the respective experiment). Statistical analysis was performed with one-way ANOVA followed by Dunnett post-hoc test.

In the control experiments, the release of CGRP and SP increased from 0.17±0.03 fmol/mg to 0.57±0.09 fmol/mg wet tissue and 1.54+0.085 fmol/mg to 2.38+0.15 fmol/mg wet tissue, respectively, in the second 8-min fraction, as a result of the electrical field stimulation. The peptide release values were still elevated in the third 8-fraction after stimulation (CGRP: 0.33±0.04 fmol/mg; SP: 2.24+0.27 fmol/mg) (FIGS. 3, 4). The absolute release in response to EFS in the second and third fractions after taking off the basal release was 0.56±0.09 fmol/mg for CGRP and 1.53+0.25 fmol/mg for SP.

Addition of CYT-1010 (10-2000 nM) to the second and third fractions significantly inhibited the stimulation-evoked CGRP and SP release, but concentration-response relationship was only observed in the smaller concentration range, between 10 and 500 nM for CGRP and 100-1000 nM for SP. In case of CGRP release, the maximal effect of 69.9% inhibition was obtained with 500 nM CYT-1010, and the 1000 and 2000 nM concentrations did not increase further the inhibitory action (66.3% and 49.1%, respectively). However, the two highest concentrations abolished, and the 100 and 500 nM significantly inhibited CGRP release in the third, post-stimulated fraction; while the 10 nM did not influence CGRP release in the third, post-stimulated fraction. For SP outflow the maximal inhibition of 71.8% was observed in the presence of the 1000 nM concentration, while 500 nM CYT-1010 evoked 64.3% inhibitory action.

Figure 5:
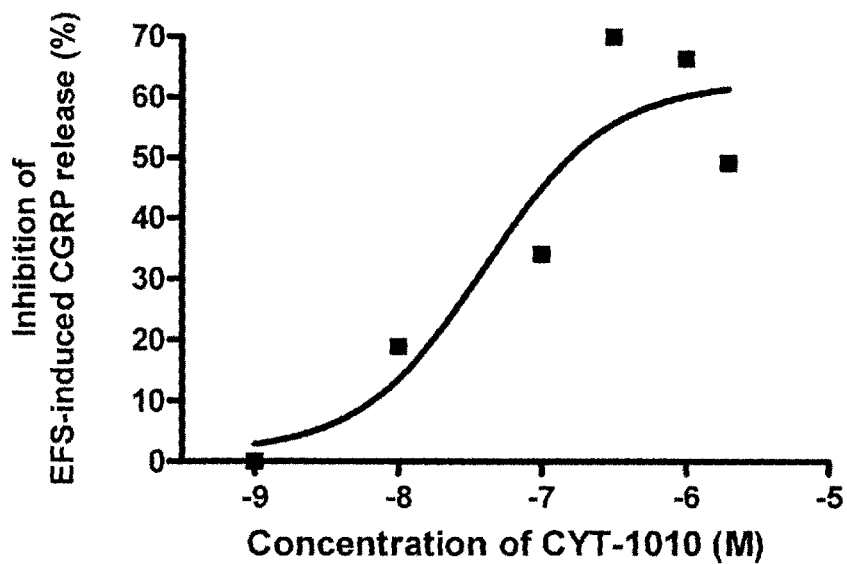
FIG. 5 shows the concentration-response curve demonstrating the inhibitory effect of CYT-1010 (10-2000 nM) on electrically-evoked release of CGRP from isolated rat tracheae. Concentration of the peptide in the basal, pre-stimulated fraction was subtracted from both the respective stimulated and post-stimulated fractions and then these values were added to calculate the absolute release. Data points represent the percentage inhibitory effects of CYT-1010 compared to the control, vehicle-treated group (n=5).
Figure 6:
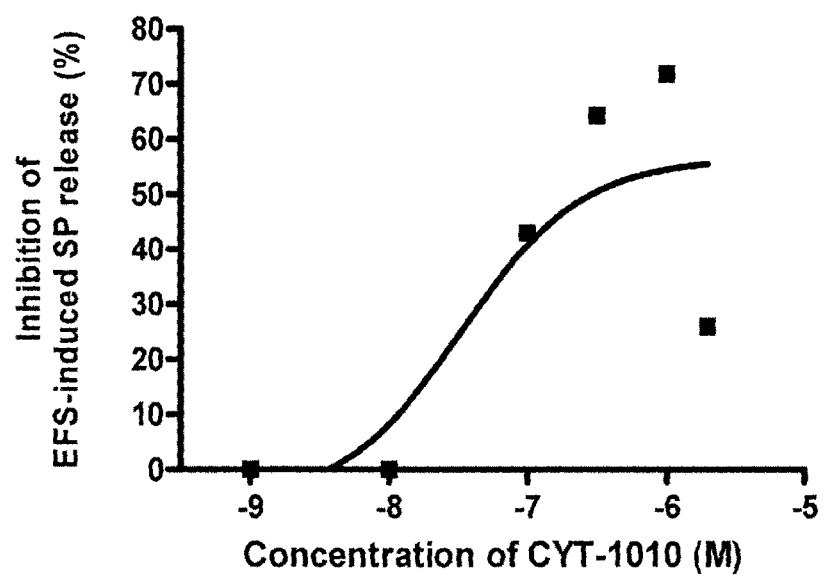
FIG. 6 shows the concentration-response curve demonstrating the inhibitory effect of CYT-1010 (10-2000 nM) on electrically-evoked release of SP from isolated rat tracheae. Concentration of the peptide in the basal, prestimulated fraction was subtracted from both the respective stimulated and poststimulated fractions and then these values were added to calculate the absolute release. Data points represent the percentage inhibitory effects of CYT-1010 compared to the control, vehicle-treated group, n=5.

When analyzing the experimental data as sigmoidal concentration-response curves via a non-linear least square curve fitting procedure, the $EC_{50}$ calculated from the best fit values proved to be 40.6 nM for CGRP and 34.0 nM for SP (FIGS. 5, 6).

TABLE 3

Release of CGRP into the incubation medium (fmol/mg wet tissue) in the pre-stimulated, stimulated and post-stimulated 8-min fractions

| Experiment | 1 | 2 | 3 | 4 | 5 | Mean | S.E.M. | % increase above baseline |
|---|---|---|---|---|---|---|---|---|
| Control (vehicle) | | | | | | | | |
| Before stimulation | 0.123 | 0.191 | 0.105 | 0.250 | 0.201 | 0.174 | 0.027 | 0.00 |
| During stimulation | 0.490 | 0.805 | 0.256 | 0.649 | 0.664 | 0.573 | 0.094 | 229.20 |
| After stimulation | 0.386 | 0.349 | 0.200 | 0.297 | 0.436 | 0.334 | 0.040 | 91.66 |
| Absolute release | 0.631 | 0.772 | 0.245 | 0.445 | 0.698 | 0.558 | 0.095 | — |
| CYT-1010 2 microM | | | | | | | | |
| Before stimulation | 0.102 | 0.231 | 0.097 | 0.148 | 0.134 | 0.142 | 0024 | 0.00 |
| During stimulation | 0.198 | 0.584 | 0.388 | 0.645 | 0.353 | 0.433 | 0.081 | 204.09 |
| After stimulation | 0.200 | 0.161 | 0.133 | 0.018 | 0.167 | 0.136 | 0.031 | −4.59 |
| Absolute release | 0.192 | 0.284 | 0.326 | 0.366 | 0.253 | 0.284 | 0.030 | — |
| CYT-1010 1 microM | | | | | | | | |
| Before stimulation | 0.262 | 0.135 | 0.108 | 0.108 | 0.102 | 0.143 | 0.030 | 0.00 |
| During stimulation | 0.510 | 0.433 | 0.170 | 0.170 | 0.161 | 0.289 | 0.076 | 101.59 |
| After stimulation | 0.386 | 0.162 | 0.130 | 0.130 | 0.121 | 0.186 | 0.051 | 29.82 |
| Absolute release | 0.371 | 0.325 | 0.083 | 0.083 | 0.077 | 0.188 | 0.066 | — |
| CYT-1010 500 nM | | | | | | | | |
| Before stimulation | 0.136 | 0.148 | 0.146 | 0.118 | 0.157 | 0.141 | 0.007 | 0.00 |
| During stimulation | 0.162 | 0.301 | 0.304 | 0.192 | 0.241 | 0.240 | 0.028 | 70.52 |
| After stimulation | 0.137 | 0.206 | 0.267 | 0.224 | 0.213 | 0.210 | 0.021 | 48.89 |
| Absolute release | 0.028 | 0.212 | 0.279 | 0.181 | 0.140 | 0.168 | 0.042 | — |
| CYT-1010 100 nM | | | | | | | | |
| Before stimulation | 0.243 | 0.129 | 0.128 | 0.138 | 0.183 | 0.164 | 0.022 | 0.00 |
| During stimulation | 0.586 | 0.281 | 0.526 | 0.390 | 0.554 | 0.468 | 0.057 | 184.81 |
| After stimulation | 0.284 | 0.135 | 0.267 | 0.231 | 0.226 | 0.229 | 0.026 | 39.26 |
| Absolute release | 0.384 | 0.159 | 0.538 | 0.344 | 0.415 | 0.368 | 0.061 | — |
| CYT-1010 10 nM | | | | | | | | |
| Before stimulation | 0.220 | 0.250 | 0.146 | 0.256 | 0.226 | 0.219 | 0.020 | 0.00 |
| During stimulation | 0.600 | 0.420 | 0.299 | 0.308 | 0.630 | 0.451 | 0.070 | 105.75 |
| After stimulation | 0.602 | 0.730 | 0.193 | 0.204 | 0.528 | 0.451 | 0.108 | 105.75 |
| Absolute release | 0.762 | 0.650 | 0.201 | 0.001 | 0.706 | 0.464 | 0.153 | — |

TABLE 4

SP Release into the incubation medium (fmol/mg wet tissue) in the pre-stimulated, stimulated and post-stimulated 8-min fractions

| Experiment | 1 | 2 | 3 | 4 | 5 | Mean | S.E.M. | % increase above baseline |
|---|---|---|---|---|---|---|---|---|
| Control (vehicle) | | | | | | | | |
| Before stimulation | 1.332 | 1.567 | 1.473 | 1.839 | 1.506 | 1.541 | 0.085 | 0.00 |
| During stimulation | 1.990 | 2.386 | 2.219 | 2.903 | 2.398 | 2.379 | 0.150 | 54.35 |
| After stimulation | 1.921 | 2.907 | 1.814 | 2.883 | 1.654 | 2.236 | 0.272 | 45.05 |
| Absolute release | 1.267 | 2.159 | 1.087 | 2.108 | 1.040 | 1.532 | 0.249 | — |
| CYT-1010 2 microM | | | | | | | | |
| Before stimulation | 2.406 | 1.582 | 2.020 | 1.132 | 1.867 | 1.801 | 0.214 | 0.00 |
| During stimulation | 3.130 | 2.398 | 2.334 | 2.078 | 4.132 | 2.814 | 0.373 | 56.23 |
| After stimulation | 2.348 | 1.531 | 2.246 | 1.543 | 1.944 | 1.922 | 0.171 | 6.72 |
| Absolute release | 0.666 | 0.765 | 0.540 | 1.357 | 2.342 | 1.134 | 0.333 | — |
| CYT-1010 1 microM | | | | | | | | |
| Before stimulation | 1.398 | 1.806 | 1.860 | 1.412 | 0.805 | 1.456 | 0.189 | 0.00 |
| During stimulation | 1.558 | 1.948 | 1.992 | 1.422 | 1.331 | 1.650 | 0.136 | 13.32 |
| After stimulation | 1.663 | 1.966 | 1.892 | 1.551 | 1.397 | 1.694 | 0.106 | 16.32 |
| Absolute release | 0.425 | 0.302 | 0.164 | 0.149 | 1.118 | 0.432 | 0.179 | — |

EXAMPLE 2

Effect of CYT-1010 on Acute Neurogenic Oedema of the Mouse Ear

This Example demonstrates that CYT-1010 significantly inhibits mustard oil-induced acute neurogenic oedema.

In the control, vehicle-treated group ear thickness increased from 312.2±4.8 μm to 348.3±7.7 μm 20 min after topical application of 5% mustard oil (11.65±1.98% swelling). This increased further to 37.83±0.83 mm by 1 h and remained relatively unchanged until 3 hours.

Figure 7:
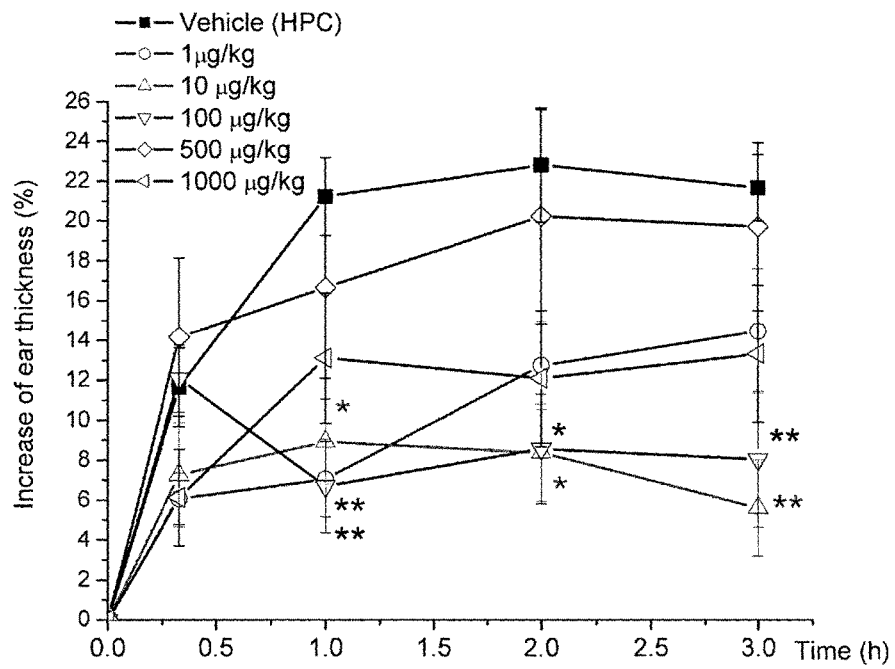
FIG. 7 shows the effect of CYT-1010 on 5% mustard oil-induced neurogenic ear swelling of the mouse. Effect of endomorphin-1 (EM-1; i.p.) on 1% mustard oil-induced neurogenic ear swelling of the mouse. In the control group saline (solvent) was applied i.p. in the same volume. Each data point represents the mean of n=8-9 experiments±s.e.m. expressed in % swelling as compared to the solvent-treated control group. *$P<0.05$; **$P<0.01$ vs. vehicle-treated control (one-way ANOVA followed by Dunnet post test).
Figure 8:
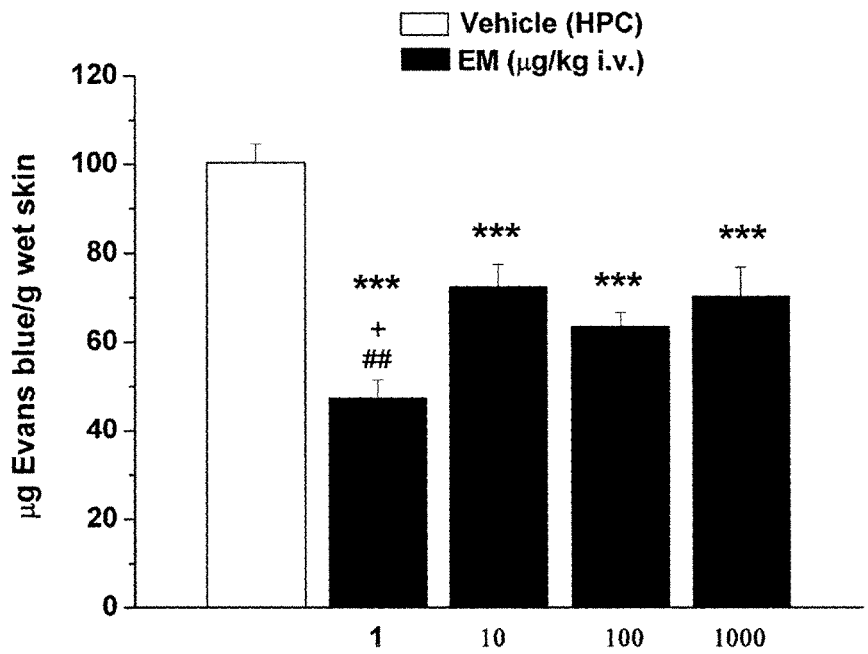
FIG. 8 shows the effect of CYT-1010 on 1% mustard oil-induced plasma protein extravasation in the acutely denervated hindpaw skin of the rat. In the control group, the vehicle (20% HPCD) was applied i.v. in the same volume. Each column shows the mean±s.e.m. of n=8 rats; ***$<0.001$ vs. vehicle-treated control group (one-way ANOVA followed by Dunnett post test); ##$P<0.01$ vs. the 10 µg/kg dose, +$P<0.05$ vs. the 1000 µg/kg dose (one-way ANOVA followed by Bonferroni's t-test).

At 1 hour, the 1, 10 and 100 μg/kg doses exerted a significant anti-edema action, although 20 minutes post induction, none of the examined CYT-1010 doses, which were administered i.v. 5 min before the induction of the inflammation, significantly inhibited mustard oil-induced ear swelling. Furthermore, the inhibitory action of 10 and 100 μg/kg CYT-1010 proved to be statistically significant at both later time points as well. The 500 and 1000 μg/kg dose did not influence ear swelling. Dose-response correlation was not observed in this model (FIG. 7). The AUC value calculated on the basis of the time course of percentage ear swelling was 55.29±4.91 units in the control, vehicle-treated group. In comparison to the control, the corresponding data in mice treated with CYT-1010 (1, 10, 100, 500 and 1000 μg/kg) were 28.99±4.60 ($P<0.05$), 28.15±3.42 ($P<0.01$), 26.55±5.51 ($P<0.01$), 52.24±9.70 (NS) and 37.25±5.72 (NS), respectively.

EXAMPLE 3

Effect of CYT-1010 on Mustard Oil-Induced Plasma Protein Extravasation in the Rat Skin This Example demonstrates that CYT-1010 significantly inhibits mustard oil-induced plasma protein extravasation.

Specifically, all of the examined CYT-1010 doses (1, 10, 100 and 1000 μg/kg, i.v.) exerted significant inhibition on 1% mustard oil-induced neurogenic plasma protein extravasation in the dorsal skin of the rat hindpaw detected by the Evans blue leakage technique. However, no dose-response correlation was observed in this model. The smallest applied dose had the greatest, 52.83% inhibitory action, while the three higher doses similarly diminished plasma protein extravasation by 27.89%, 36.76% and 29.90%, respectively. The inhibitory action of 1 μg/kg CYT-1010 was significantly greater than those of the 10 and 100 μg/kg doses (FIG. 6).

TABLE 5

Evans blue leakage in the rat hindpaw skin (μg/g wet skin) in response to topical administration of 1% mustard oil

| | Control | CYT-1010 i.v. | | | |
|---|---|---|---|---|---|
| | (vehicle) | 1 μg/kg | 10 μg/kg | 100 μg/kg | 1000 μg/kg |
| 1 left | 129.10 | 48.52 | 91.18 | 52.19 | 76.56 |
| 1 right | 89.03 | 44.06 | 61.48 | 49.21 | 54.68 |
| 2 left | 99.63 | 33.73 | 77.24 | 80.28 | 63.41 |
| 2 right | 92.07 | 63.04 | 87.67 | 71.20 | 55.85 |
| 3 left | 86.96 | 42.27 | 79.89 | 54.84 | 66.07 |
| 3 right | 74.19 | 3.46 | 77.63 | 83.92 | 85.40 |
| 4 left | 80.28 | 41.04 | 87.14 | 49.09 | 79.34 |
| 4 right | 102.49 | 31.69 | 108.49 | 54.86 | 154.03 |
| 5 left | 103.06 | 46.87 | 73.59 | 59.74 | 74.05 |
| 5 right | 129.17 | 49.44 | 65.69 | 88.54 | 88.00 |
| 6 left | 97.34 | 47.62 | 78.05 | 56.89 | 62.92 |
| 6 right | 120.26 | 77.51 | 94.66 | 75.00 | 55.80 |
| 7 left | 109.70 | 53.72 | 36.25 | 56.81 | 67.62 |
| 7 right | 118.11 | 48.91 | 51.07 | 63.41 | 57.47 |
| 8 left | 85.49 | 59.80 | 41.10 | 68.93 | 37.45 |
| 8 right | 87.80 | 65.26 | 46.38 | 49.74 | 46.10 |
| Mean | 100.29 | 47.31 | 72.34 | 63.42 | 70.30 |
| SEM | 4.24 | 4.14 | 5.13 | 3.25 | 6.55 |

As demonstrated in Examples 1-3, electrical field stimulation (EFS) evoked more than 3-fold elevation of CGRP release compared to its basal outflow. The total absolute peptide release was decreased by 70% and 66% in response to adding CYT-1010 into the organ bath during and after stimulation in 500 nM and 1 μM concentrations, respectively. Also, electrically-induced SP release was 54% in the stimulated and 45% in the post-stimulated fractions, respectively. The total release was significantly diminished by 64% and 72% in the presence of 500 nM and 1 μM CYT-1010. When analyzing the data as sigmoidal concentration-response curves via a non-linear least square curve fitting procedure, the $EC_{50}$ calculated from the best fit values proved to be 40.6 nM for CGRP and 34.0 nM for SP. A concentration-response relationship was observed in the concentration range of 10-500 nM for CGRP and 100-1000 nM for SP.

Mustard oil-induced acute neurogenic ear swelling of the mouse was significantly reduced by 1 µg/kg, 10 µg/kg and 100 µg/kg i.v. doses of CYT-1010. A similar significant anti-inflammatory effect was found on mustard oil-evoked plasma protein extravasation in the rat skin by i.v. pretreatment with 1-1000 µg/kg CYT-1010; the lowest dose exerted the greatest effect, almost 60% inhibitory action.

Based on these results it can be concluded that CYT-1010 effectively attenuates neurogenic inflammatory responses in which the inhibition of sensory neuropeptide release is likely to be involved. Since this type of inflammation is not affected by the presently available non-steroidal anti-inflammatory/analgesic drugs and high doses of corticosteroids induce only a moderate inhibition, this stable and highly potent EM-1 analog provides a novel treatment of inflammatory conditions where pain and nociceptor activation play a pivotal role.

EXAMPLE 4

Effects of Filtered and Non-Filtered CYT-1010 on Mustard Oil-Induced Acute Neurogenic Ear Swelling in Mice This Example demonstrates that filtration of CYT-1010 moderately decreases the inhibitory action of CYT-1010. This inhibitory effect was markedly less in comparison with filtered vehicle controls.

Materials and Methods

CYT-1010 (synthetic cyclized endomorphin-1 analog; FP014; Lot #: 080811-R2; Bottle H22; MW:684), was purchased from AmbioPharm, Inc. (North Augusta, S.C. 29812). Additional materials include: 2-hydroxypropyl-βcyclodextrin (HPCD; Batch No. L-36/07), purchased from Cyclolab Ltd., Budapest, Hungary; urethane, purchased from Spektrum 3D, Debrecen, Hungary; allylisothiocyanate (mustard oil), paraffin oil, purchased from Szkarabeusz Ltd., Pécs, Hungary, and sterile syringe filters (PVDF; 0.2 µm; TR-200507; Lot. 134831), purchased from OlimPeak, Teknokroma, Barcelona, Spain.

Preparation of Solutions and Suspensions

Stock solution of the 100 µg/ml concentration of CYT-1010 (5.5 ml) was prepared fresh every experimental day with 20% hydroxypropyl-βcyclodextrin (HPCD) dissolved in sterile distilled water, shaken properly and sonicated. The vehicle was 20% HPCD dissolved in sterile distilled water. Further dilutions of the compound for the smaller administered doses were made with this vehicle. The applied concentrations were filtered through a 0.2 µm sterile teflon filter. This 100 µg/ml solution was opalescent directly after preparation, but it cleared up 1 hour later at C. The lower concentrations looked clear immediately. Non-filtered solutions were administered in the same concentrations in the parallel groups for comparison. Three doses of both the filtered and non-filtered CYT-1010 solutions (1, 10 and 100 µg/kg; 0.1 ml/10 g from the 0.1, 1 and 10 µg/ml solutions) were administered i.v. 5 min before the induction of the inflammation. Animals of the control group were treated with the same volume of the HPCD after or without the same filtration procedure.

Mustard Oil-induced Acute Neurogenic Inflammation in the Mouse Ear

Experimental Model

Mice were anaesthesized with urethane (1.2 g/kg i.p.) to achieve a long-lasting deep anaesthesia and minimize respiratory depression. Ten µl of 5% mustard oil dissolved in paraffin oil was smeared on both sides of both ears. Mustard oil in this concentration selectively activates Transient Receptor Potential A1 (TRPA1) on capsaicin-sensitive peptidergic sensory nerves and induces the release of sensory neuropeptides (Banvolgyi et al., 2004). The released calcitonin gene-related peptide (CGRP) and tachykinins such as substance P (SP) in the innervated area evoke vasodilatation and plasma protein extravasation collectively called acute neurogenic inflammation (Helyes et al., 1997, 2001, 2006; Borzsei et a., 2008).

Protocol

CYT-1010 (1, 10 and 100 µg/kg; 0.1 ml/10 g from the 0.1, 1, 10 µg/ml solutions) was administered i.v. 5 min before the induction of the inflammation by mustard oil smearing. Mice in the control group were treated with the same volume of the vehicle, 20% HPCD dissolved in sterile distilled water There were 8 mice in each experimental group, and 9 in the 1 µg/kg filtered CYT-1010 dose group CYT-1010-treated vehicle-treated control group.

Animals 65 male CD1 mice (25-35 g) were divided into 8 experimental groups: Group 1: non-filtered vehicle-treated controls (n=8); Group 2: non-filtered 1 µg/kg CYT-1010 (n=8); Group 3: non-filtered 10 µg/kg CYT-1010 (n=8); Group 4: non-filtered 100 µg/kg CYT-1010 (n=8); Group 5: filtered vehicle-treated controls (n=8); Group 6: filtered 1 µg/kg CYT-1010 (n=9); Group 7: filtered 10 µg/kg CYT-1010 (n=8); and Group 8: filtered 100 µg/kg CYT-1010 (n=8).

This study was undertaken in blocks with 16-17 mice per occasion. The whole set of data was obtained during 4 days (12, 13, 16, 22 Apr. 2010). There were 2 or 3 solvent-treated rats every day and the remaining 12 animals were randomised to receive each treatment.

Investigational Technique Measurement of Mouse Ear Swelling with Micrometry

The diameter of the ear was measured with an engineers' micrometer before the treatment and 4 times during the 3 h-examination period (20 min, 1 h, 2 h and 3 h). Edema was expressed in % compared to the initial control values (Banvolgyi et al., 2004; Borzsei et al., 2008). The compound was administered i.v. 5 min before mustard oil smearing in 3 doses (1, 10, 100 µg/kg) in separate groups after sterile filtration or without filtration. Animals of the control group were treated with the same volume of the vehicle Statistical Analysis Results are expressed as the mean±s.e.m. Statistical significance was performed with one-way ANOVA followed by Dunnett's post-hoc test (modified t-test) when the data of the CYT-1010-treated groups were compared to the respective vehicle-treated controls at certain time points. The areas under the time-dependent percentage ear swelling curves (AUC) were also calculated and analyzed with the same statistics to compare the whole edema responses of the CYT-1010-treated mice during the 3 h-experimental period to the respective control group. *p<0.05 was considered to be significant. Microsoft Excel was used for storing the individual data and preparing the worksheets, GrapPad-Prism5 for statistical analysis and Origin 7.0 for making the graphs.

Ethics

All experimental procedures were carried out according to the 1998/XXVIII Act of the Hungarian Parliament on Animal Protection and Consideration Decree of Scientific Procedures of Animal Experiments (243/1988) and complied with the recommendations of the International Association for the Study of Pain and the Helsinki Declaration. The studies were approved by the Ethics Committee on Animal Research of Pécs University according to the Ethical Codex of Animal Experiments and licensee was given (licensee No.: BA 02/2000-11-2006).

Effect of Non-Filtered CYT-1010 on Acute Neurogenic Edema of the Mouse Ear

Figure 9:
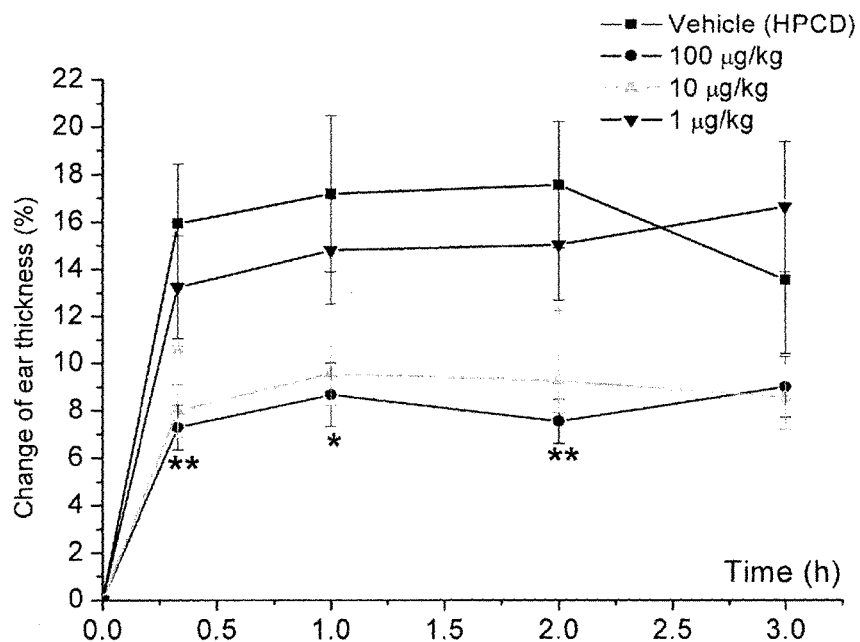
FIG. 9 shows the effect of non-filtered i.v. CYT-1010 solution on 5% mustard oil-induced neurogenic ear swelling of the mouse. In the control group the 20% HPCD vehicle was applied i.v. in the same volume without filtration. Each data point represents the mean of n=8-9 mice±s.e.m. expressed in % swelling as compared to the control group. *$P<0.05$; **$P<0.01$ vs. vehicle-treated control (one-way ANOVA followed by Dunnett's post-test).

In the control, non-filtered vehicle-treated group ear thickness increased from 312.50±4.70 μm to 361.25±6.05 μm 20 min after topical application of 5% mustard oil (15.94±2.51% swelling). This remained relatively stable during 2 hours, then started to minimally decrease. The 10 μg/kg and 100 μg/kg CYT-1010 i.v. doses without filtration administered 5 min before the induction of the inflammation significantly inhibited mustard oil-induced ear swelling 20 min later, and these inhibitory actions were observed until the 2 hour time point. Although the edema-decreasing action of 10 μg/kg CYT-1010 was not statistically significant at 1 h with the Dunnett's post test we used for data analysis, the inhibitory tendency was clearly seen. The 1 μg/kg dose did not significantly diminish ear swelling, although a minimal reduction was observed in the first 2 hours. Dose-response correlation was not found in this model (FIG. 9). The AUC value calculated on the basis of the time course of percentage ear swelling was 44.02±6.97 units in the control, HPCD vehicle-treated group. In comparison to the control, the corresponding data in mice treated with CYT-1010 (1, 10 and 100 μg/kg) were 40.33±5.32 (NS), 24.21±2.75 ($P<0.05$), 21.71±1.72 ($P<0.01$), respectively.

Effect of Filtered CYT-1010 on Acute Neurogenic Edema of the Mouse Ear

Figure 10:
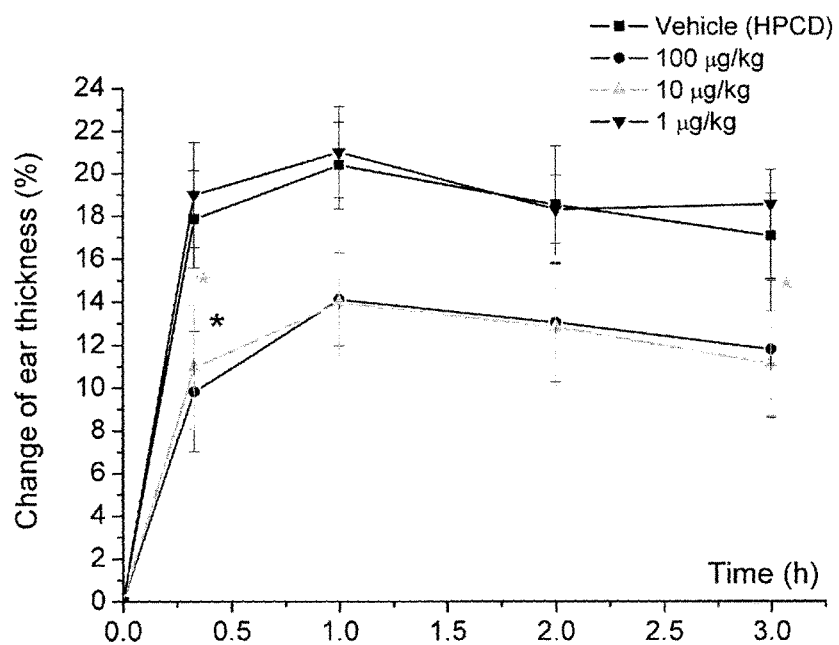
FIG. 10 shows the effect of filtered i.v. CYT-1010 solution on 5% mustard oil-induced neurogenic ear swelling of the mouse. In the control group the 20% HPCD vehicle was applied i.v. in the same volume after filtration. Each data point represents the mean of n=8 mice±s.e.m. expressed in % swelling as compared to the control group. *$P<0.05$; **$P<0.01$ vs. vehicle-treated control (one-way ANOVA followed by Dunnett's post-test).

In the control, filtered HPCD vehicle-treated group ear thickness increased from 294.17±4.17 μm to 339.17±7.63 μm 20 min after topical application of 5% mustard oil (17.85±2.01% swelling). This remained almost unchanged throughout the 3 hour-examination period. The 10 μg/kg and 100 μg/kg doses of filtered CYT-1010 solutions administered i.v. 5 min before the induction of the inflammation inhibited significantly mustard oil-induced ear swelling 20 min later, but statistically significant anti-edema effect compared to the vehicle-treated control group was only observed for the 10 μg/kg dose at the 3 h time point. However, the inhibitory actions of the filtered solution compared to the respective concentrations of the non-filtered compounds was not significantly different. The filtered 1 μg/kg dose did not influence ear swelling. Similarly to the actions of the non-filtered compound, dose-response correlation was not observed in this experimental series either (FIG. 10). The AUC value calculated on the basis of the time course of percentage ear swelling was 50.04±6.96 units in the control, filtered HPCD vehicle-treated group. In comparison to the control, the corresponding data in mice treated with the filtered CYT-1010 (1, 10 and 100 μg/kg) were 51.47±6.93 (NS), 33.68±3.79 (NS), and 33.97±5.62 (NS), respectively.

In this Example 4, mustard oil-induced acute neurogenic ear swelling of the mouse was significantly reduced by 10 μg/kg and 100 μg/kg doses of CYT-1010 injected i.v. without filtration. The extent of the inhibition was about 50% in both cases, there was no dose-response correlation. A minimal inhibitory tendency was also observed in the 1 μg/kg dose in the first 2 hours. The HPCD vehicle after filtrating through a 0.2 μm sterile filter did not show any difference compared to the non-filtered controls. Administration of the two higher CYT-1010 doses after filtration exerted moderate inhibition. Compared to the respective vehicle-treated controls statistically significant differences were only observed at the 20 min time point and at 3 h in case of the 10 μg/kg dose. Analysing the areas under the curves did not show any significant differences between any group, although a clear inhibitory tendency was observed for both the 10 and 100 CYT-1010 treatment. The filtered 1 μg/kg dose did not have any effect.

Based on these results it can be concluded that filtration moderately decreases the inhibitory action of CYT-1010 in this model. Although this effect was not significantly smaller than that of the respective non-filtered formulations, it was markedly less in comparison with the filtered vehicle controls.

All patents, patent applications, provisional applications, and publications referred to or cited herein are incorporated by reference in their entirety, including all figures and tables, to the extent they are not inconsistent with the explicit teachings of this specification.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A method for treating a human subject to reduce neurogenic inflammation, wherein said method comprises administering, intravenously, to a human subject in need of treatment of neurogenic inflammation, an effective amount of the acetate salt of SEQ ID NO:13.

2. The method, according to claim 1, further comprising administering an anti-inflammatory agent selected from the group consisting of a steroidal compound, hydrocortisone, a non-steroidal anti-inflammatory compound, acetylsalicylic acid (aspirin), ibuprofen, acetaminophen, and indomethacin, wherein the anti-inflammatory agent is administered before, during, or after the administration of said peptide or salt thereof.

* * * * *

UNITED STATES PATENT AND TRADEMARK OFFICE
CERTIFICATE OF CORRECTION

PATENT NO.        : 10,441,625 B2
APPLICATION NO.   : 16/035274
DATED             : October 15, 2019
INVENTOR(S)       : Theodore E. Maione et al.

Page 1 of 1

It is certified that error appears in the above-identified patent and that said Letters Patent is hereby corrected as shown below:

In the Specification

Column 18:
Table 3, Line 43, "… 0142 0024 0.00" should read -- 0142 0.024 0.00 --.

Column 19:
Table 4, Line 8, "Before stimulation 1.332 1.567" should read -- Before stimulation 1.322 1.567 --.

Column 21:
Line 58, "1 hour later at C." should read -- 1 hour later at 4 C. --.

Signed and Sealed this
Second Day of June, 2020

Andrei Iancu
*Director of the United States Patent and Trademark Office*